(12) United States Patent
Yu et al.

(10) Patent No.: US 11,300,500 B2
(45) Date of Patent: Apr. 12, 2022

(54) SAMPLE DETECTION DEVICE AND SAMPLE DETECTION METHOD BY USING THE SAME

(71) Applicant: ALIGNED GENETICS, INC., Anyang-si (KR)

(72) Inventors: Alexey Dan Chin Yu, Anyang-si (KR); Neon Cheol Jung, Anyang-si (KR); Keunchang Cho, Anyang-si (KR)

(73) Assignee: Aligned Genetics, Inc., Anyang-si (KR)

( * ) Notice: Subject to any disclaimer, the term of this patent is extended or adjusted under 35 U.S.C. 154(b) by 0 days.

(21) Appl. No.: 17/095,505

(22) Filed: Nov. 11, 2020

(65) Prior Publication Data

US 2021/0140875 A1 May 13, 2021

(30) Foreign Application Priority Data

Nov. 12, 2019 (KR) ........................ 10-2019-0144492

(51) Int. Cl.
*G01N 21/21* (2006.01)
*A61B 5/00* (2006.01)
(Continued)

(52) U.S. Cl.
CPC ........... *G01N 21/21* (2013.01); *A61B 5/0059* (2013.01); *A61B 5/0071* (2013.01);
(Continued)

(58) Field of Classification Search
CPC . A61B 5/0059; A61B 5/0071; A61B 2576/00; G02B 21/0076; G02B 21/0092;
(Continued)

(56) References Cited

U.S. PATENT DOCUMENTS 3,971,952 A * 7/1976 Inbar .................. G01N 21/6445
250/461.2
5,943,129 A * 8/1999 Hoyt .................. G01N 21/6445
356/318
(Continued)

FOREIGN PATENT DOCUMENTS

JP 2017102266 A * 6/2017 ......... G02B 21/0052
KR 10-2001-0090592 A 10/2001
(Continued)

*Primary Examiner* — Gordon J Stock, Jr.
(74) *Attorney, Agent, or Firm* — Knobbe Martens Olson & Bear LLP

(57) ABSTRACT

A sample detection device includes a first polarizer configured to allow part of incident light to pass therethrough by polarizing the incident light, a stage disposed on a path of light having passed the first polarizer, the stage allowing a sample to be seated thereon, a second polarizer configured to polarize light and a detection unit configured to detect light having passed the second polarizer and to generate a detection signal. The first polarizer allows first polarized light oscillating in a first direction to proceed toward the sample when the incident light reaches the first polarizer. Emission light is emitted by an excitation of the sample when the first polarized light reaches the sample. The second
(Continued)

polarizer allows second polarized light oscillating in a second direction to proceed toward the detection unit when the emission light reaches the second polarizer.

12 Claims, 8 Drawing Sheets

(51) Int. Cl.
    *G01N 21/64*     (2006.01)
    *G02B 21/00*     (2006.01)

(52) U.S. Cl.
    CPC ..... *G01N 21/6445* (2013.01); *G01N 21/6458* (2013.01); *G02B 21/0092* (2013.01); *A61B 2576/00* (2013.01); *G01N 2021/218* (2013.01)

(58) Field of Classification Search
    CPC ............. G02B 21/16; G01N 2021/218; G01N 2021/6463; G01N 2021/6495; G01N 2021/6497; G01N 21/21; G01N 21/64; G01N 21/6402; G01N 21/6428; G01N 21/643; G01N 21/6445; G01N 21/6447; G01N 21/645; G01N 21/6452; G01N 21/6456; G01N 21/6458; G01N 21/6486
    See application file for complete search history.

(56) References Cited

U.S. PATENT DOCUMENTS

| | | | |
|---|---|---|---|
| 10,073,045 B2* | 9/2018 | Barak | G02B 21/002 |
| 2003/0219754 A1* | 11/2003 | Oleksy | C12Q 2563/173 |
| | | | 435/6.11 |
| 2005/0094147 A1* | 5/2005 | Yaroslavsky | A61B 5/444 |
| | | | 356/417 |
| 2007/0243521 A1* | 10/2007 | Zuckerman | A61B 5/7278 |
| | | | 435/4 |
| 2008/0074649 A1* | 3/2008 | Levenson | G06K 9/6289 |
| | | | 356/73 |
| 2010/0108873 A1* | 5/2010 | Schwertner | G02B 21/367 |
| | | | 250/252.1 |
| 2010/0108908 A1* | 5/2010 | Klunder | B82Y 15/00 |
| | | | 250/458.1 |
| 2015/0293337 A1* | 10/2015 | Matsumoto | G02B 21/06 |
| | | | 359/250 |
| 2016/0299057 A1* | 10/2016 | Casas | G02B 21/367 |
| 2017/0363472 A1* | 12/2017 | Abdulhalim | G01J 3/2823 |
| 2021/0063310 A1* | 3/2021 | Shirokawa | G01N 21/6456 |

FOREIGN PATENT DOCUMENTS

| | | |
|---|---|---|
| KR | 10-2019-0063524 A | 6/2019 |
| WO | WO 2016/098581 A1 | 6/2016 |

* cited by examiner

*FIG.2A* *FIG.2B* *FIG.2C*
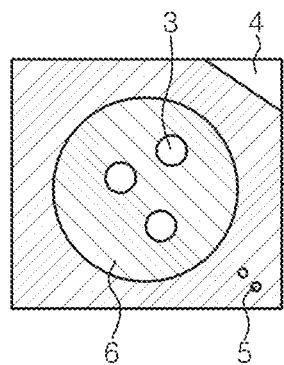 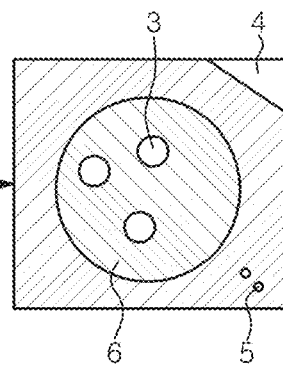 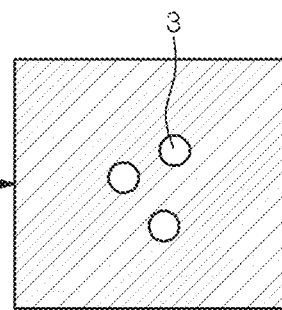

SAMPLE DETECTION DEVICE AND SAMPLE DETECTION METHOD BY USING THE SAME

CROSS-REFERENCE TO RELATED APPLICATIONS

This application is based on and claims priority from Korean Patent Application No. 10-2019-0144492, filed on Nov. 12, 2019, the disclosure of which is incorporated herein in its entirety by reference for all purposes.

BACKGROUND

Technical Field

The present disclosure relates to a sample detection device and a sample detection method using the same.

Description of Related Technology

In general, a fluorescent microscope uses the principle that a sample itself such as a bacteria or protein emits fluorescence when a fluorescent substance having fluorescence absorbs light having a specific wavelength. After the sample is treated with a fluorescent substance (fluorescent dye), the sample may be emitted with light having an absorption wavelength of the fluorescent substance and observed through radiation light emitted from the sample. Such a fluorescent microscope is widely used to observe a sample such as a biochip because it can obtain a clear image compared to a general optical microscope.

In such a fluorescent microscope system, sharpness of a sample shape (relative intensity I to a background) is proportional to the square of a numerical aperture (NA) and inversely proportional to a transverse magnification (M) of a device. Therefore, the sharpness of an image of the sample may rapidly decrease as the magnification increases. This may be expressed by an equation as follows.

$$I \propto (NA^2/M)^2$$

SUMMARY

The present disclosure provides a sample detection device that can obtain a clear image of a sample by lowering the magnification of the device and reducing background noise.

In accordance with an aspect of the present disclosure, there is provided a sample detection device comprising: a first polarizer configured to allow first polarized light which is a part of incident light to pass therethrough by polarizing the incident light; a stage disposed on a path of the first polarized light, the stage allowing a sample to be disposed thereon; a second polarizer configured to polarize light; and a detection unit configured to detect second polarized light having passed the second polarizer and to generate a detection signal, wherein the first polarizer allows the first polarized light oscillating in a first direction to proceed toward the sample when the incident light reaches the first polarizer, wherein emission light is emitted by an excitation of the sample when the first polarized light reaches the sample, and wherein the second polarizer allows the second polarized light oscillating in a second direction to proceed toward the detection unit when the emission light reaches the second polarizer.

The sample detection device may further comprise: a reflective member configured to reflect the first polarized light to proceed toward the sample; and a first lens configured to refract reflection light reflected from the reflective member to proceed toward the sample.

Alternatively, the sample detection device may further comprise: a reflective member configured to reflect the emission light to proceed toward the detection unit; and a first lens disposed on a path of the first polarized light and configured to refract the emission light to proceed toward the reflective member.

Further, the sample detection device may further comprise: a second lens configured to refract the second polarized light to proceed toward the detection unit, wherein a distance between the second lens and the detection unit is identical to a distance between the first lens and the stage.

The second polarizer may be oriented to block part of the emission light proceeding toward the second polarizer.

The first direction may be orthogonal to the second direction.

The emission light may be fluorescence, and the detection unit may detect the fluorescence emitted from the sample.

The sample detection device may further comprise: an actuator configured to change a relative position of the stage with respect to at least one of the second lens and the detection unit.

The sample detection device may further comprise: a controller configured to correct an image of the sample, wherein the controller obtains a first image of the sample when the sample is disposed at a predetermined position, obtains a second image of the sample when a relative position of the stage with respect to at least one of the second lens and the detection unit is changed, and obtains an corrected image of the sample based on the first image and the second image.

In accordance with another aspect of the present disclosure, there is provided a sample detection method using the sample detection device described above, comprising: emitting the incident light to the first polarizer to allow the first polarized light oscillating in the first direction to proceed toward the sample; and detecting the second polarized light to obtain an image of the sample based on the second polarized light.

The sample detection method may further comprise: obtaining a first image of the sample when the stage on which the sample is disposed is disposed at a first observation position; obtaining a second image of the sample when the stage is disposed at a second observation position different from the first observation position; and obtaining a corrected image of the sample based on the first image and the second image.

The sample detection method may further comprise: moving the stage through an actuator to move a position of the sample from the first observation position to the second observation position.

The sample detection method may further comprise giving a first weight to the first image and a second weight to the second image; wherein, the corrected image of the sample is corrected based on the first image given the first weight and the second image given the second weight.

In accordance with still another aspect of the present disclosure, there is provided a non-transitory computer-readable storage medium including computer-executable instructions, wherein the instructions, when executed by a processor, cause the processor to perform a sample detection method using the sample detection device described above, comprising: emitting the incident light to the first polarizer to allow the first polarized light oscillating in the first direction to proceed toward the sample; and detecting the second polarized light to obtain an image of the sample based on the second polarized light.

According to embodiments of the present disclosure, a clear image of a sample may be obtained by reducing background noise, while using an objective lens having a low magnification of 10 times equal to or less than.

BRIEF DESCRIPTION OF THE DRAWINGS

FIG. 2A, FIG. 2B and FIG. 2C are diagrams respectively illustrating a first image, a second image, and a corrected image obtained using the sample detection device of FIG. 1.

DETAILED DESCRIPTION

Figure 1:
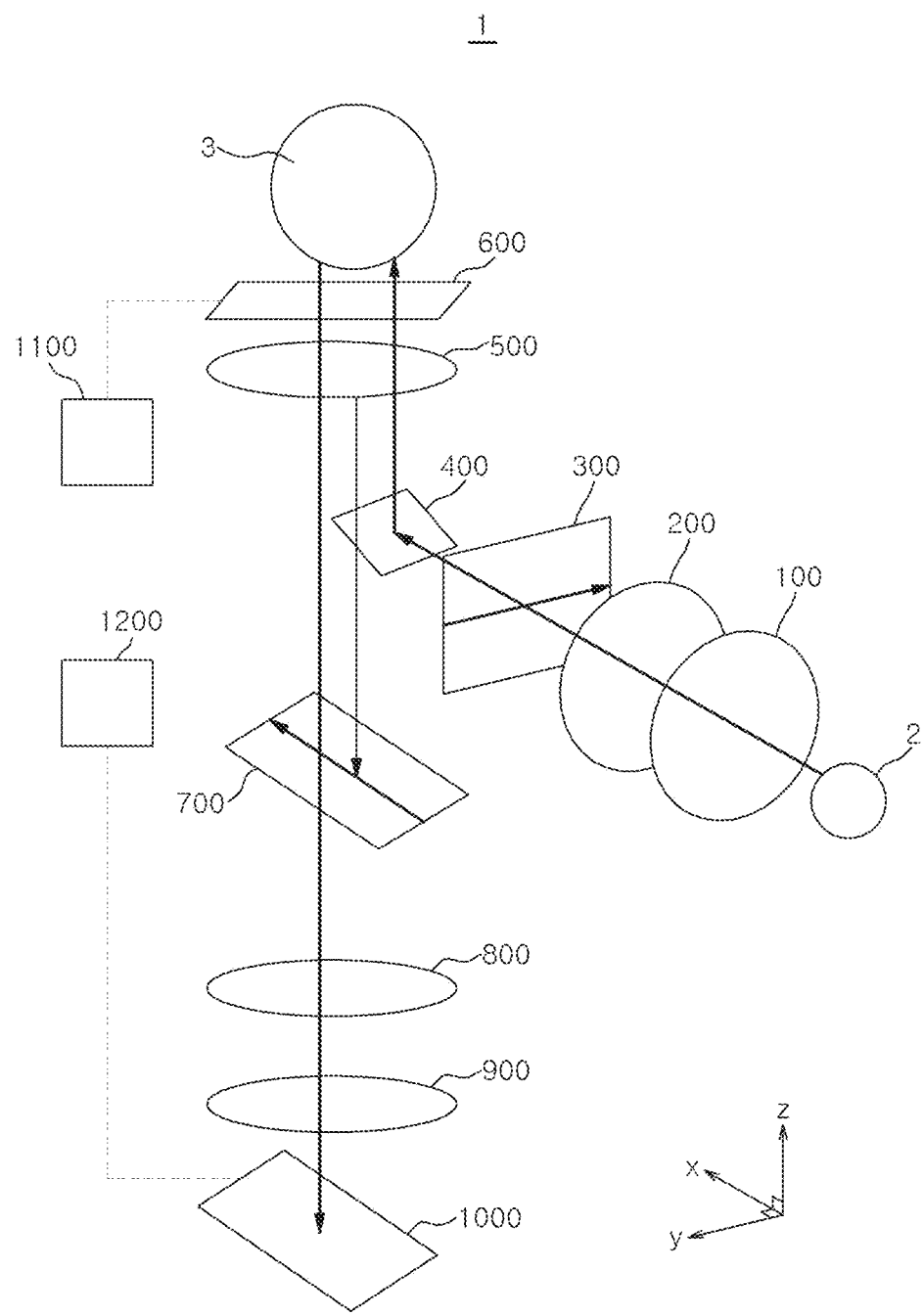
FIG. 1 is a conceptual diagram schematically showing a sample detection device according to an embodiment of the present disclosure.

Meanwhile, the image of the sample obtained through the fluorescent microscope may include background noise. For example, the background noise may be a defect of the device, a noise signal from a camera, an appearance such as a frame of the device, ambient light, background fluorescence, and the like. In addition, the background noise may occur due to backscattering of optical or mechanical elements to a detector. Such background noise may be a factor that lowers the sharpness of the sample image. Accordingly, there is a need for a device that can obtain a clear sample image by lowering the magnification of the device and reducing background noise.

The advantages and features of exemplary embodiments of the present disclosure and methods of accomplishing them will be clearly understood from the following description of the embodiments taken in conjunction with the accompanying drawings. However, the present disclosure is not limited to those embodiments and is implemented in various forms. It is noted that the embodiments are provided to make a full disclosure and also to allow those skilled in the art to know the full scope of the present disclosure.

In the following description, well-known functions and/or configurations will not be described in detail if they would unnecessarily obscure the features of the disclosure. Further, the terms to be described below are defined in consideration of their functions in the embodiments of the disclosure and vary depending on a user's or operator's intention or practice. Accordingly, the definition is made on a basis of the content throughout the present disclosure.

A sample detection device 1 according to an embodiment of the present disclosure may obtain an enlarged image of a sample 3 using light emitted from a light source 2.

In this disclosure, the light source 2 may be an object that can emit light. For example, the light source 2 may be a light emitting diode (LED), a laser diode (LD), a halogen lamp, a mercury lamp, a xenon lamp, or the like, and light emitted from the light source 2 may have a wavelength of 300 nm equal to or more than and 800 nm equal to or less than. Light emitted from the light source 2 may proceed toward the sample detection device 1.

In addition, the sample 3 may be an object to be observed by the sample detection device 1. The sample 3 may absorb light having a specific range of wavelength and may re-emit absorbed light. Meanwhile, the sample 3 may be coated with a fluorescent dye. In other words, the sample 3 may have a concept including an observation target such as a biological tissue and a fluorescent dye. When ultraviolet rays or short-wavelength visible light is emitted to the fluorescent dye-coated sample 3, dye molecules of the sample may emit light. In this way, when light having a wavelength of a predetermined range is emitted to the fluorescent material, fluorescence in the range of visible light or near-infrared ray emitted may be emitted. The sample 3 may have an optical characteristic of anisotropy and may double refract incident light to emit light.

Hereinafter, the sample detection device 1 according to an embodiment of the present disclosure will be described with reference to FIG. 1.

The sample detection device 1 may emit light emitted from the light source 2 to the sample 3 and detect light emitted from the sample 3 to observe the sample 3. When observing the sample 3, the sample detection device 1 may obtain a clearer image of the sample 3 by removing optical interference caused by external light or an object other than the sample 3. For example, the sample detection device 1 may be a fluorescence detection device. Such a fluorescence detection device detects a small amount of a fluorescent substance, thereby observing a distribution of the fluorescent substance present in cells or samples that are difficult to observe.

Further, the sample detection device 1 may obtain a clear image of the sample 3 by reducing background noise at a low magnification (e.g., a magnification of 0.5:1). A magnification of a first lens 500 provided in the sample detection device 1 may be in a range from 0.5 to 10 times. In addition, a numerical aperture (NA) of the first lens 500 provided in the sample detection device 1 may be in a range from 0.1 to 0.7 when a magnification which is obtained by combining the first lens 500 and a second lens 900 is 1:1.

The sample detection device 1 may include a homogenizer 100, an optical filter 200, a first polarizer 300, a reflective member 400, a first lens 500, a stage 600, and a second polarizer 700, a radiation filter 800, a second lens 900, a detection unit 1000, an actuator 1100, and a controller 1200.

The homogenizer 100 may provide a portion to which light emitted from the light source 2 is incident. The homogenizer 100 may allow rays of light (light bundle) passing through the homogenizer 100 to be parallel. In other words, the rays of light emitted from the light source 2 may be parallel and uniform, while passing through the homogenizer 100. Light passing through the homogenizer 100 may proceed toward the optical filter 200.

The optical filter 200 may allow light emitted from the light source 2 to selectively pass therethrough. In other words, the optical filter 200 may allow light having a wavelength of a predetermined range among light, emitted from the light source 2 and having passed through the homogenizer 100, to pass therethrough. The optical filter 200 may block light having a wavelength of a range different from the wavelength of the predetermined range. Here, the wavelength of the predetermined range refers to a wavelength of the range that the sample 3 may absorb. For example, the range of the wavelength, which may be absorbed by the sample 3, may be 300 nm equal to or more than and 800 nm equal to or less than. In addition, the optical filter 200 may be an excitation filter allowing light having a range of wavelength that can excite fluorescent dye of the sample 3 to pass therethrough. The optical filter 200 may extend in a direction orthogonal to a direction in which light emitted from the light source 2 proceeds. Light having passed the optical filter 200 may proceed toward the first polarizer 300.

The first polarizer 300 may allow part of incident light to pass therethrough by polarizing the incident light emitted from the light source 2. In other words, the first polarizer 300 may allow first polarized light oscillating in a first direction to proceed toward the sample when the incident light reaches the first polarizer. The first polarizer 300 may block part of the incident light oscillating in a direction different from the first direction. Here, the first direction refers to any one direction orthogonal to the direction in which the incident light proceeds. For example, when the incident light proceeds in the x direction as shown in FIG. 1, the first direction may be a ±y direction orthogonal to the x direction. In addition, the first polarizer 300 may be, for example, a linear polarizer. The first polarizer 300 may be disposed to face the optical filter 200, and the first polarized light may proceed toward the reflective member 400.

The reflective member 400 may reflect the first polarized light. The reflective member 400 may reflect the first polarized light to proceed in a direction different from the direction in which the first polarized light proceeds. In other words, the reflective member 400 may reflect the first polarized light to proceed toward the stage 600. For example, the direction in which the reflection light reflected from the reflective member 400 proceeds is orthogonal to the direction in which the first polarized light proceeds.

The reflective member 400 may be a beam splitter, for example, a dichroic mirror that can allow light having a wavelength of a predetermined range to be selectively transmitted therethrough. In other words, the reflective member 400 may allow light having a wavelength of a predetermined range to be transmitted therethrough and reflect light having a wavelength of the range different from the wavelength of the predetermined range. The reflective member 400 may also reflect the light having the wavelength of the predetermined range and allow light having the wavelength different from the wavelength of the predetermined range to be transmitted therethrough.

The first lens 500 may refract the reflection light to be concentrated toward the stage 600. In other words, the first lens 500 may refract the reflection light and allow it to proceed toward the sample 3. For example, the first lens 500 may be an objective lens. The first lens 500 may be disposed on a path of the reflection light. In addition, a distance between the first lens 500 and the stage 600 is identical to a distance between the second lens 900 and the detection unit 1000. Since the first lens 500 and the second lens 900 of the same specification are symmetrically arranged, the optical distortion of each lens is canceled out to prevent distortion of an image obtained by the detection unit 1000. In particular, such optical distortion is a phenomenon that occurs remarkably when a lens having a high NA is applied to an optical system having a low magnification, which is a factor that prevents a high sensitivity optical system with a low magnification.

Meanwhile, the first lens 500 may reflect light reflected from the reflective member 400 toward the second polarizer 700. As such, the light reflected from the first lens 500 may pass through the reflective member 400 and travel toward the second polarizer 700. The first lens 500 may be formed of, for example, quartz, glass, plastic, or polymer.

The stage 600 may provide a space in which the sample 3 is seated. The stage 600 may allow refraction light, refracted by the first lens 500 and proceeding toward the sample 3, to pass therethrough. The stage 600 may be disposed on a path of the refraction light. In other words, the stage 600 may be disposed between the first lens 500 and the sample 3.

Meanwhile, the refraction light may excite the sample 3 and may be reflected from the sample 3. In addition, the refraction light may be reflected from either the sample 3 or the stage 600. In this way, and the refraction light reflected from the sample 3 or the stage 600 may proceed toward the second polarizer 700.

In addition, the sample 3 may be excited when the first polarized light, having reflected from the reflective member 400 and then refracted by the first lens 500, reaches the sample. In this way, when the sample 3 is excited, the sample may emit emission light having a wavelength of a predetermined range. Here, the emission light emitted from the sample 3 may proceed toward the first lens 500. In addition, the emission light may pass through the first lens 500 and proceed toward the second polarizer 700.

A direction of oscillation of the emission light may be changed due to anisotropy of the sample 3. For example, the emission light may oscillate in a second direction different from the first direction in which the first polarized light oscillates. The sample 3 may have a surface having a different reflectivity depending on a direction of light emitted to the sample 3, and the oscillation direction of the light may be changed due to such anisotropy. The degree to which the oscillation direction of light changes may vary depending on a structure, thickness, and non-radiation transition of the sample 3. Meanwhile, in a case where the sample 3 is coated with a fluorescent dye, when the refraction light is emitted to the sample 3, fluorescence may be emitted from the sample 3.

Due to the anisotropy of the sample, the emission light may oscillate in a direction different from the direction of the refraction light emitted to the sample 3. The emission light may include light oscillating along the second direction. Here, the second direction may be any one direction orthogonal to a direction in which the emission light proceeds. Meanwhile, unlike the case described above, the emission light may be unpolarized light. Accordingly, even if light proceeding toward the sample 3 oscillates in the first direction, the emission light may oscillate in a plurality of directions.

Meanwhile, the first direction of the present disclosure may be defined based on certain two reference directions (e.g., two of the x, y, and z directions), and the second direction may be defined based on one of the certain two reference directions. In addition, in the drawing, the first direction may be y direction orthogonal to a z direction and an x direction of FIG. 1, and the second direction may be the x direction of FIG. 1. However, the technical idea of the present disclosure is not limited thereto.

The second polarizer 700 may allow part of the emission light to pass therethrough by polarizing the emission light proceeding toward the second polarizer 700 In other words, the second polarizer 700 may allow second polarized light oscillating in a second direction to proceed toward the detection unit 1000 when the emission light reaches the second polarizer 700. The second polarizer 700 may block part of the emission light oscillating in a direction different from the second direction. Here, the second direction refers to any on direction orthogonal to the direction in which the emission light proceeds. In addition, the second polarizer 700 may be, for example, a linear polarizer. The second polarized light may proceed toward the radiation filter 800.

Meanwhile, the second polarizer 700 may block noise light other than the emission light. In other words, the second polarizer 700 may block the noise light oscillating in the direction which is identical to the first direction. For example, the second polarizer 700 may block the noise light reflected from the first lens 500 and then proceeding toward the second polarizer 700. In addition, the second polarizer 700 may block the noise light reflected from one of the sample 3 and the stage 600 and then proceeding toward the second polarizer 700. In this way, since the second polarizer 700 blocks the noise light, unnecessary background noise is prevented from being detected by the detection unit 1000. Meanwhile, since the emission light (e.g., fluorescent signal) does not pass through the first polarizer 300, it may not be blocked by the second polarizer 700 and may pass through the second polarizer 700 to proceed the radiation filter 800 and the detection unit 1000.

The radiation filter 800 may allow the second polarized light to selectively pass therethrough. In other words, the radiation filter 800 may allow light having a wavelength of a predetermined range in the light passing through the second polarizer 700 to pass therethrough and block light having a wavelength different from the wavelength of the predetermined range. For example, a range of the wavelength allowed to pass through the radiation filter 800 may be 400 nm equal to or more than and 900 nm equal to or less than. Light passing through the radiation filter 800 may proceed toward the second lens 900.

The second lens 900 may refract the second polarized light having passed the radiation filter 800 to proceed toward the detection unit 1000. The second lens 900 may have a low magnification so as to improve sharpness (intensity relative to the background) of the image detected by the detection unit 1000 and widen an observation field of the detection unit 1000. Further, a distance between the second lens 900 and the detection unit 1000 is identical to a distance between first lens 500 and the stage 600. In this way, since the first lens 500 and the second lens 900 are configured to have the same specifications and arranged to be symmetrical to each other, distortion that occurs in the image of the sample 3 obtained by the detection unit 1000 may be 100% reduced theoretically.

In addition, although it is described above that the specifications (focal length, NA, magnification, etc.) of the first lens 500 and the second lens 900 are the same, the first lens 500 and the second lens 900 may be configured such that focal lengths thereof are slightly different but the other specifications are the same, thereby changing the magnification, while minimizing optical distortion. For example, by combining the first lens 500 and the second lens 900, the optical magnification of the sample detection device 1 may be selected as 0.5 to 10 times. However, if the difference in the focal length between the first lens 500 and the second lens 900 is too large, optical distortion due to the difference in focal length is not canceled out even if the two lenses have the same specifications, and thus they cannot be used practically.

The second polarized light may proceed to the detection unit 1000.

The detection unit 1000 may generate a detection signal by detecting the second polarized light and may transmit the generated detection signal to the controller 1200. For example, the detection unit 1000 may be a detection sensor. This detection signal may include image information detected by the detection unit 1000. Further, the detection signal may include background noise that may interfere with formation of an accurate image of the sample 3.

The actuator 1100 may change a relative position of the stage 600 with respect to at least one of the second lens 900 and the detection unit 1000. Accordingly, the actuator 1100 may also change a position of the sample 3 seated on the stage 600 with respect to at least one of the second lens 900 and the detection unit 1000. By moving the stage 600, the actuator 1100 may move the position of the sample 3 from a first observation position (a) to a second observation position (b). The position of the sample 3 changed by the actuator 1100 may be in a microscale unit.

The controller 1200 may obtain an image of the sample 3 based on the detection signal from the detection unit 1000. In addition, the controller 1200 may correct the obtained image of the sample 3 to obtain a clearer image of the sample 3. The controller 1200 may be implemented by a measurement device such as a computing device including a microprocessor, a sensor, etc., and a memory, and an implementation method thereof is obvious to those skilled in the art, and thus a detailed description thereof will be omitted.

The controller 1200 may obtain a first image of the sample 3 when the sample 3 is disposed at a predetermined position based on a detection signal generated by the detection unit 1000. As shown in FIG. 2A, the position of the sample 3 when the first image is obtained is defined as the first observation position (a).

When the first image is obtained by the controller 1200, the stage 600 is moved to a position different from the first observation position (a). In other words, a relative position of the stage 600 with respect to at least one of the second lens 900 and the detection unit 1000 is changed through the actuator 1100. Here, as shown in FIG. 2B, the position of the sample 3 seated on the stage 600 whose position has been changed is defined as the second observation position (b), and the second observation position (b) may be apart from the first observation position (a) by a predetermined distance. Here, the predetermined distance may be a distance larger than a size of the sample 3 (e.g., individual cells, fluorescent beads, and points formed on the surface of the slide).

In addition, when the relative position of the stage 600 with respect to at least one of the second lens 900 and the detection unit 1000 is changed, the controller 1200 may obtain a second image based on a detection signal generated from the detection unit 1000.

The controller 1200 may obtain an image of the sample 3 corrected based on the first image and the second image. Here, the controller 1200 may remove background noise signals that may interfere with the image formation of the sample 3 from the detection signals transmitted from the detection unit 1000. These background noise signals may be factors interfering with the observation of the sample 3, such as ambient light 4, a defect 5 of the device, an object (not shown) such as a frame of the device, and background fluorescence 6. Such a background noise signal may be detected by the detection unit 1000 in the same manner when obtaining the first image and the second image even if the position of the sample 3 changes.

The controller 1200 may subtract background noise obtained when obtaining the first image from background noise obtained when obtaining the second image in order to obtain the corrected image (see FIG. 2C) of the sample 3. In other words, a portion common to the background noise obtained when obtaining the second image may be removed from the background noise obtained when obtaining the first image. Accordingly, when the background noise is removed through the controller 1200, the corrected image of the sample 3, clearer than the image of the sample 3 obtained when the first image is obtained, may be obtained.

Figure 3:
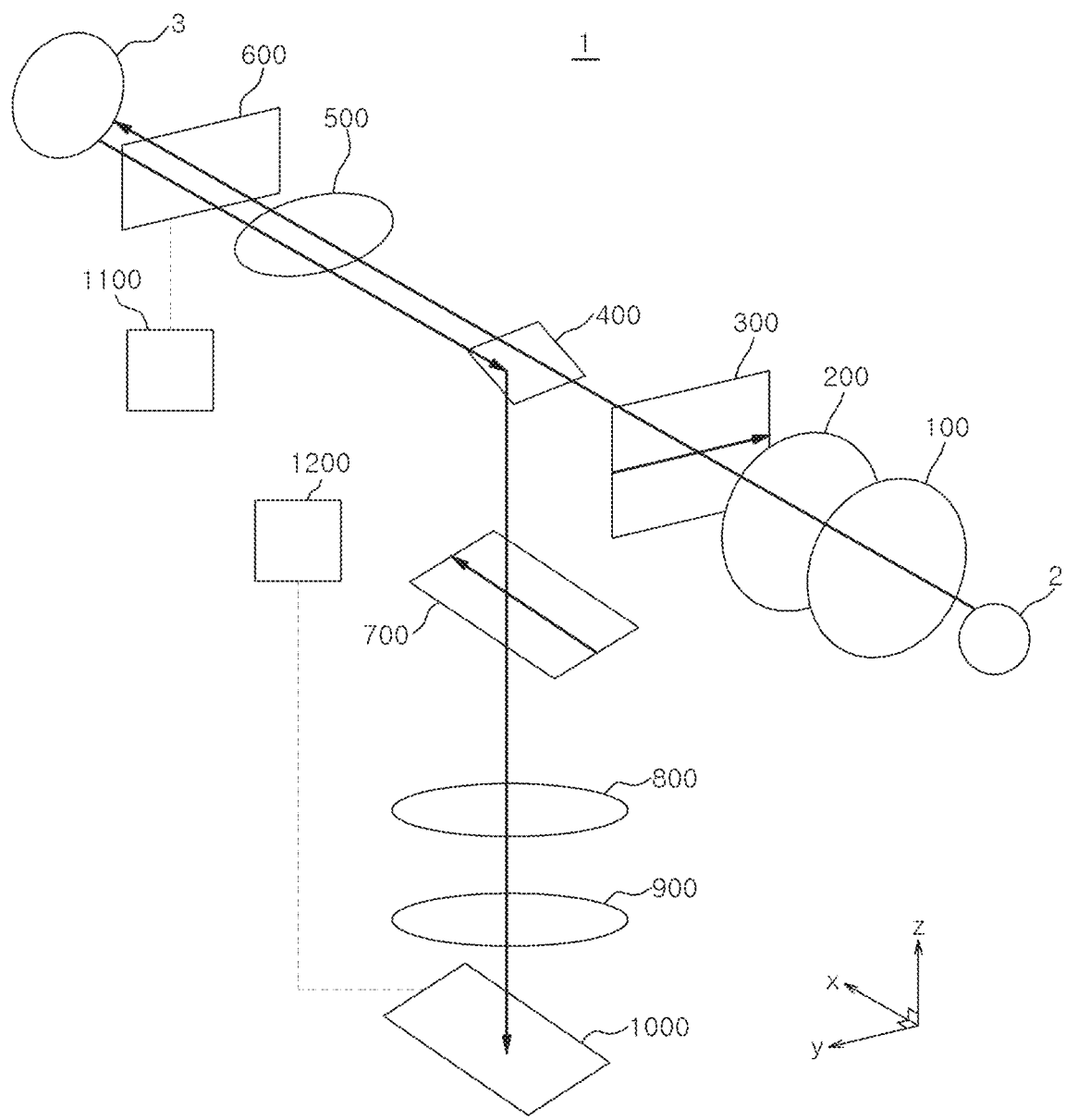
FIG. 3 is a conceptual diagram schematically showing a sample detection device according to another embodiment of the present disclosure.

Meanwhile, according to another embodiment of the present disclosure, as shown in FIG. 3, the positions of the stage 600 on which the sample 3 is seated and the first lens 500 may be changed. The stage 600 and the first lens 500 may be disposed on a path of the first polarized light.

Referring to FIG. 3, the reflective member 400 according to another embodiment of the present disclosure may allow the first polarized light to be transmitted therethrough so that the first polarized light proceed toward the first lens 500 and the sample 3. In addition, the reflective member 400 may reflect the emission light emitted from the sample 3 to proceed toward the detection unit 1000.

The first lens 500 may refract the first polarized light to proceed toward the sample 3. The first lens 500 may be disposed on a path of the first polarized light proceeding toward the sample 3. In addition, the first lens 500 may allow the emission light to pass therethrough. The emission light having passed through the first lens 500 may be reflected by the reflective member 400 and detected by the detection unit 1000.

Hereinafter, a sample detection method using the sample detection device 1 described above will be described.

Figure 4:
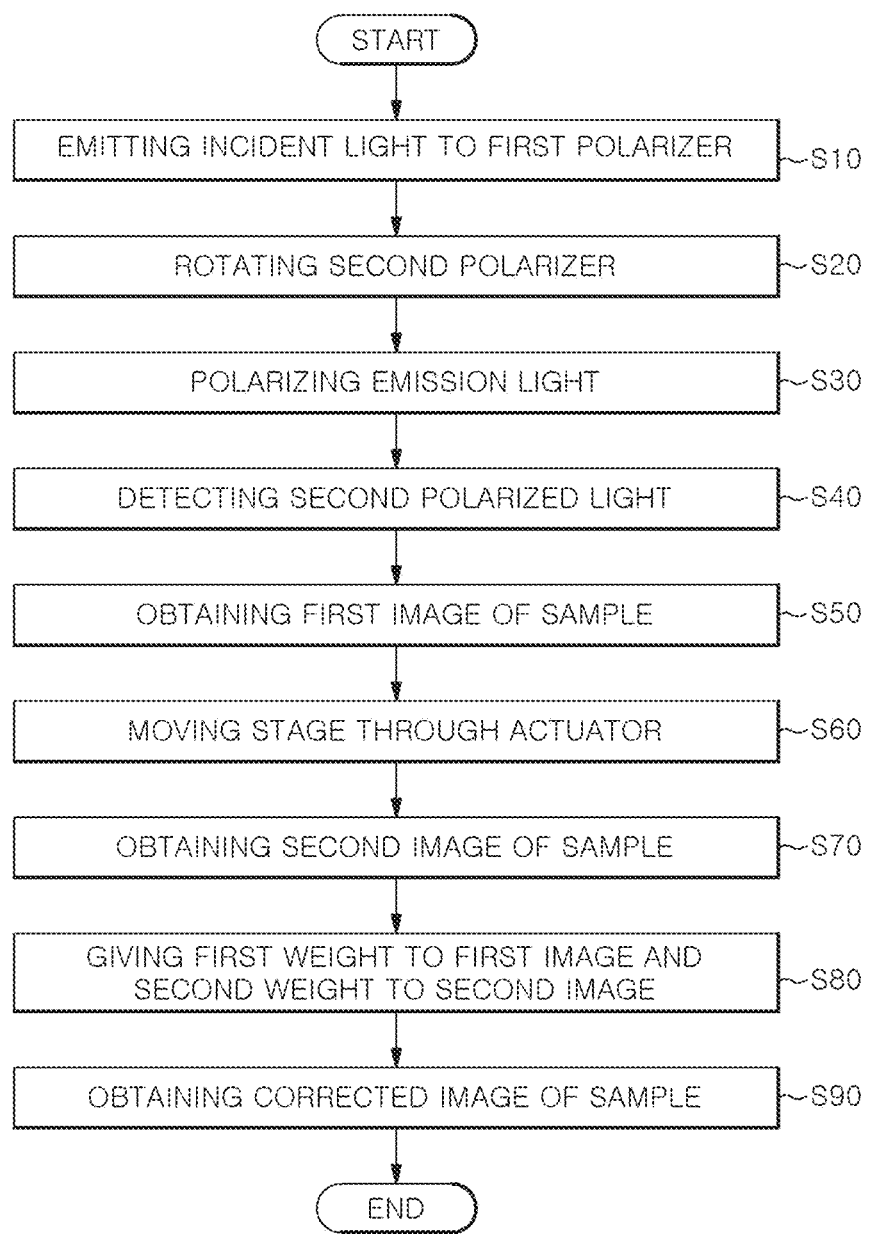
FIG. 4 is a flowchart showing a sample detection method according to embodiments of the present disclosure.

Referring to FIG. 4, in the sample detection method, an image of the sample 3 may be obtained using the sample detection device 1, and a clear image of the sample 3 may be obtained by correcting the obtained image.

The light source 2 emits incident light to the first polarizer 300. The first polarizer 300 may allow first polarized light, which is a part of the incident light to pass therethrough by polarizing the incident light. The first polarizer 300 allows the first polarized light oscillating in a first direction having passed through the first polarizer 300, to proceed toward the sample 3 (S10).

The second polarizer 700 may rotate to allow a part of the emission light, oscillating in a second direction different from the first direction, to pass therethrough (S20).

The emission light proceed toward the second polarizer 700. The second polarizer 700 may allow second polarized light to pass therethrough by polarizing the emission light. The second polarizer 700 allows the second polarized light oscillating in the second direction to proceed toward the detection unit 1000 (S30).

The detection unit 1000 may detect the second polarized light to obtain an image of the sample based on the second polarized light (S40)

The controller 1200 may obtain a first image of the sample 3 when the stage 600 on which the sample 3 is seated is disposed at a first observation position (S50).

The actuator 1100 may move the stage to move position of the sample 3 from the first observation position to the second observation position (S60).

The controller 1200 may obtain a second image of the sample 3 when the stage 600 is disposed at a second observation position (S70).

The controller 1200 may give a first weight to the first image and a second weight to the second image (S80). For example, when the first image is clearer than the second image, the controller 1200 may multiply the first image by the first weight which is greater than 1 so that the intensity of the first image increases. The controller 1200 multiply the second image by the second weight which is less than 1 so that the intensity of the second image decreases.

The controller 1200 may obtain a corrected image of the sample 3 based on the first image given the first weight and the second image given the second weight (S90).

Hereinafter, the effect of the sample detection device 1 having the configuration as described above will be described.

The sample detection device 1 according to the embodiments of the present disclosure has an effect of obtaining a clear image of the sample 3 by obtaining high sensitivity without optical distortion at a low magnification and reducing background noise. Since the intensity of the sample detection device 1 is proportional to the square of the numerical aperture (NA) of the first lens 500 corresponding to an objective lens and inversely proportional to the magnification M of the first lens 500 according to the following equation. Therefore the magnification may be lowered as the numerical aperture (NA) increases.

$$I \propto (NA^2/M)^2$$

However, in the related art, there is a limitation in increasing the NA at a low magnification due to severe optical distortion. For example, in the case of the related art, when the magnification is 1×, the NA is about 0.04, but in the case of the sample detection device 1 according to the embodiment of the present disclosure, when the magnification of the first lens 500 is 1×, the NA is 0.35, and thus, according to the above equation, the embodiment of the present disclosure may have a sharpness improved by 5000 times equal to or more than compared to the related art. In addition, as another example, if the related art has the same NA as that of the sample detection device 1 according to the embodiments of the present disclosure, while having a magnification of 10 times that of the sample detection device 1 according to the embodiments of the present disclosure, the embodiment of the present disclosure based on the above equation may have a sharpness 100 times improved compared to the related art.

In addition, when a low magnification is used as in the embodiments of the present disclosure, a larger area may be observed at a time, significantly reducing time for imaging. For example, if the magnification is reduced to 1/10, only images 1/100 sheets may need to be obtained to observe the same area, and thus, time for imaging may be 100 times faster than the related art.

Hereinafter, superiority of sharpness I of the sample 3 obtained using the sample detection device of the related art and the sample detection device 1 according to embodiments of the present disclosure through an experiment will be described.

Figure 5:
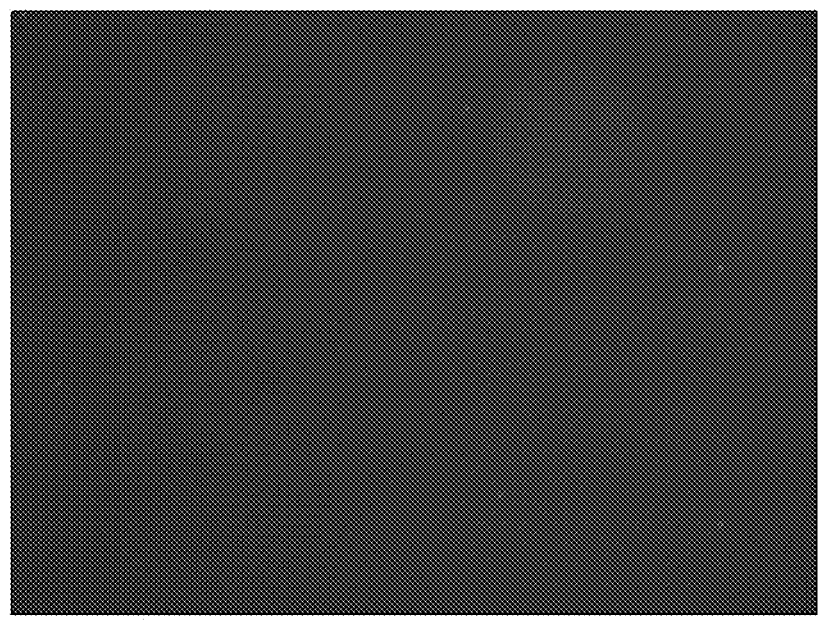
FIG. 5 is an image of blood cells obtained using a sample detection device of the related art.
Figure 6:
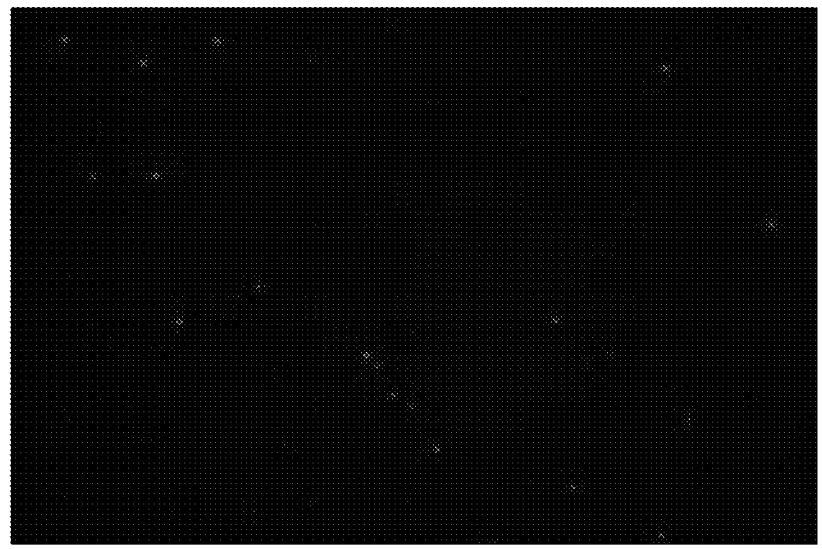
FIG. 6 is an image of blood cells obtained using a sample detection device according to embodiments of the present disclosure.

Referring to FIGS. 5 and 6, FIG. 5 shows an image of a sample obtained when blood cells are detected using the sample detection device of the related art, and FIG. 6 shows an image of a sample obtained when blood cells are detected using the sample detection device 1 according to embodiments of the present disclosure. The sample detection device 1 may detect a large area of a sample at a low magnification and has an effect of obtaining the image of the sample 3 clearer than the image of the sample obtained by the sample detection device of the related art, by reducing background noise.

Figure 7:
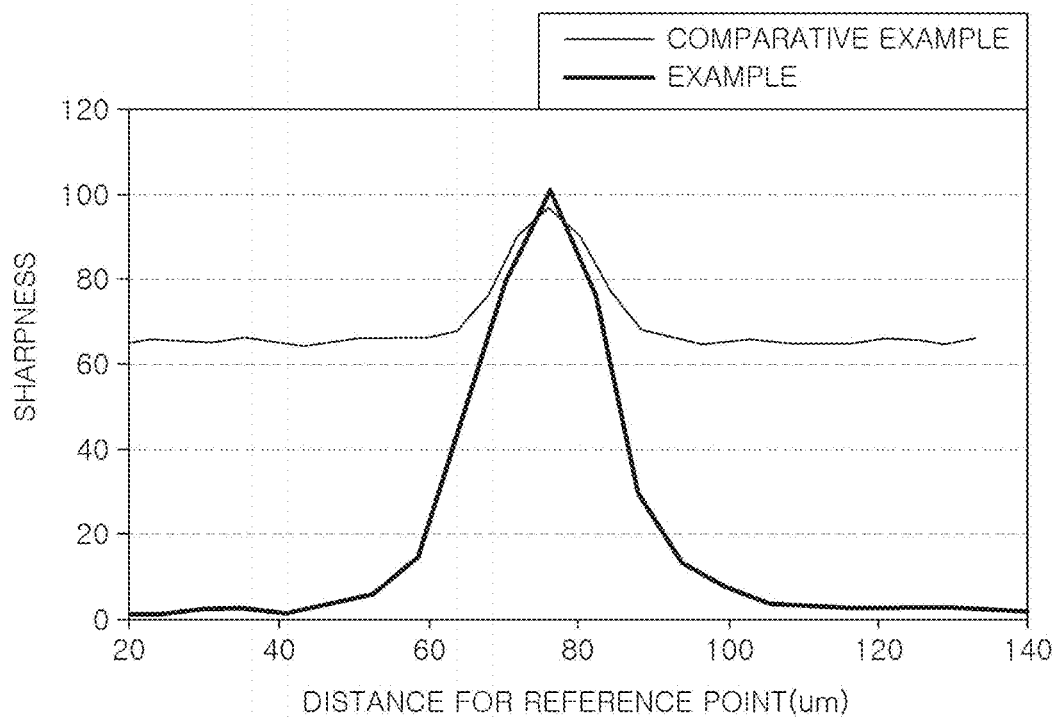
FIG. 7 is a graph showing comparison of sharpness over distance when a sample detection device according to embodiments of the present disclosure and a sample detection device of the related art detect blood cells.

FIG. 7 is a graph showing a comparison of signal sensitivity over distance to a certain reference point when the sample detection device according to an example of the present disclosure and the sample detection device of the related art (comparative example) detect blood cells. Referring to FIG. 7, when detecting blood cells, the sample detection device 1 according to the example of the present disclosure has an effect of detecting a higher signal sensitivity than that of the sample detection device of the related art to obtain an image. Meanwhile, the comparative example in the graph of FIG. 7 is an experimental result of a sample detection device without a polarizer and without image correction.

Figure 8:
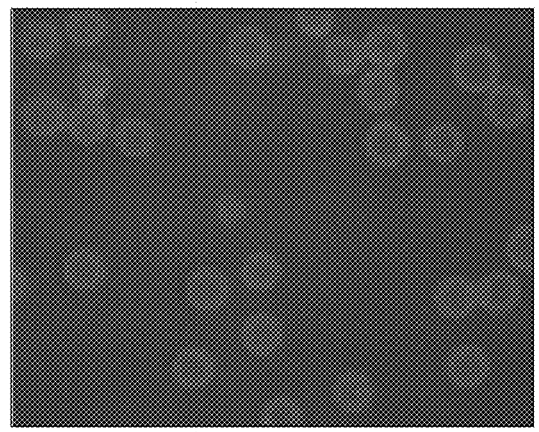
FIG. 8 is an image of a fluorescent bead obtained using a sample detection device of the related art.
Figure 9:
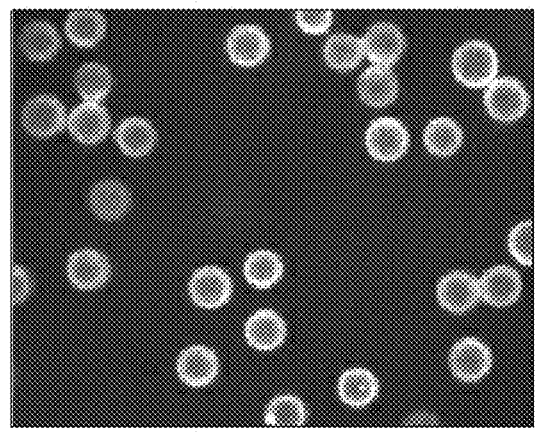
FIG. 9 is an image of a fluorescent bead obtained using a sample detection device according to embodiments of the present disclosure.

Referring to FIGS. 8 and 9, FIG. 8 is an image of a sample obtained when fluorescent beads are detected using the sample detection device of the related art and FIG. 9 is an image of a sample obtained when fluorescent beads are detected using the sample detection device 1 according to the example of the present disclosure. Such a sample detection device 1 may detect a large area of a sample at a low magnification and have an effect of obtaining an image of the sample 3 clearer than the image of the sample obtained by the sample detection device of the related art, by reducing background noise.

Figure 10:
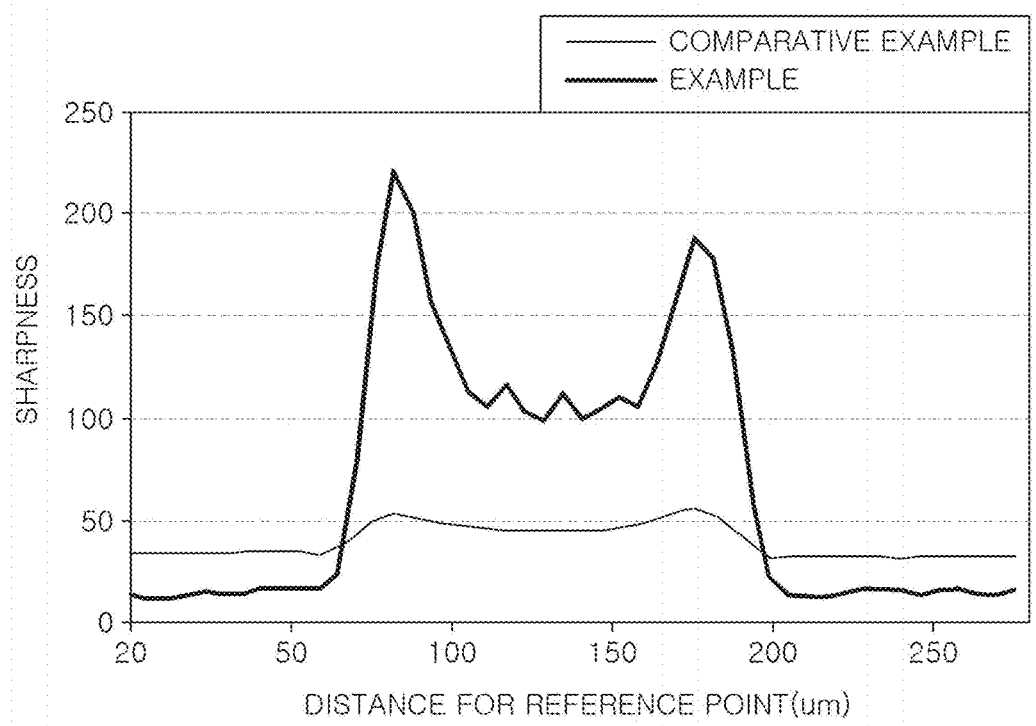
FIG. 10 is a graph showing comparison of sharpness over distance when a sample detection device according to embodiments of the present disclosure and a sample detection device of the related art detect fluorescent beads.

FIG. 10 is a graph showing comparison of signal sensitivity over distance to a certain reference point when the sample detection device according to the example of the present disclosure and the sample detection device of the related art (comparative example) detect fluorescent beads. Referring to FIG. 10, when detecting the fluorescent beads, the sample detection device 1 according to the example of the present disclosure has an effect of obtaining an image by detecting a higher signal sensitivity than the sample detection device of the related art. In the graph of FIG. 10, the comparative example is an experiment result of a sample detection device without a polarizer and without image correction.

Combinations of steps in the flowcharts of the present disclosure can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions specified in the steps of the flowchart.

These computer program instructions may also be stored in a computer usable or computer readable memory that can direct a computer or other programmable data processing apparatuses to function in a particular manner, such that the instructions stored in the computer usable or computer readable medium can produce an article of manufacture including instructions which implement the function specified in the steps of the flowcharts.

The computer program instructions may also be loaded onto a computer or other programmable data processing apparatuses to cause a series of operational steps to be performed on the computer or other programmable apparatuses to produce a computer implemented process such that the instructions which execute on the computer or other programmable apparatuses provide processes for implementing the functions specified in the steps of the flowcharts.

Each step in the flowchart may represent a module, segment, or portion of code, which comprises one or more executable instructions for implementing the specified logical function(s). It should also be noted that, in some alternative implementations, the functions noted in the step may occur out of the order noted in the figures. For example, two steps shown in succession may, in fact, be executed substantially concurrently, or the steps may sometimes be executed in the reverse order, depending upon the functionality involved.

The above description is merely exemplary description of the technical scope of the present disclosure, and it will be understood by those skilled in the art that various changes and modifications can be made without departing from original characteristics of the present disclosure. Therefore, the embodiments disclosed in the present disclosure are intended to explain, not to limit, the technical scope of the present disclosure, and the technical scope of the present disclosure is not limited by the embodiments. The protection scope of the present disclosure should be interpreted based on the following claims and it should be appreciated that all technical scopes included within a range equivalent thereto are included in the protection scope of the present disclosure.

The national research and development project related to this application are as follows:

[The R&D Grant #1 that has supported this invention]
[Registration number] 20009860
[Department] Ministry of Trade, Industry and Energy, Korea
[Research management institution] Korea Evaluation Institute of Industrial Technology
[Project name] Bioindustry Core Technology Development
[Title] Development of blood cell analysis system based on machine learning image analysis for minimal residual disease
[Contribution] 50%
[Supervising institute] Aligned Genetics, Inc.
[Research Period] 1 Apr. 2020~31 Dec. 2024
[The R&D Grant #2 that has supported this invention]
[Registration number] 10067407
[Department] Ministry of Trade, Industry and Energy, Korea
[Research management institution] Korea Evaluation Institute of Industrial Technology
[Project name] Bioindustry Core Technology Development
[Title] Development of high throughput organoid clearing system and 3D imaging system for drug
[Contribution] 50%
[Supervising institute] Aligned Genetics, Inc.
[Research Period] 1 Jul. 2016~30 Jun. 2021

What is claimed is:
1. A sample detection device comprising:
   a first polarizer configured to allow first polarized light which is a part of incident light to pass therethrough by polarizing the incident light;
   a stage disposed on a path of the first polarized light, the stage allowing a sample to be disposed thereon;
   a second polarizer configured to polarize light;
   a reflective member configured to reflect the first polarized light to proceed toward the sample;

a first lens configured to refract reflection light reflected from the reflective member to proceed toward the sample;

a detection unit configured to detect second polarized light having passed the second polarizer and to generate a detection signal;

a second lens configured to refract the second polarized light to proceed toward the detection unit; and a controller configured to correct an image of the sample, wherein the first polarizer is configured to allow the first polarized light oscillating in a first direction to proceed toward the sample when the incident light reaches the first polarizer, wherein emission light is configured to be emitted by an excitation of the sample when the first polarized light reaches the sample, wherein the second polarizer is configured to allow the second polarized light oscillating in a second direction to proceed toward the detection unit when the emission light reaches the second polarizer, and wherein the controller is configured to obtain a first image of the sample when the sample is disposed at a predetermined position, obtain a second image of the sample when a relative position of the stage with respect to at least one of the second lens and the detection unit is changed, and obtain a corrected image of the sample based on the first image and the second image.

2. The sample detection device of claim 1, wherein the first lens is disposed on a path of the first polarized light and configured to refract the emission light to proceed toward the reflective member.

3. The sample detection device of claim 1, wherein the emission light is fluorescence, and wherein the detection unit is configured to detect the fluorescence emitted from the sample.

4. The sample detection device of claim 1, wherein a distance between the second lens and the detection unit is identical to a distance between the first lens and the stage.

5. The sample detection device of claim 4, further comprising:

an actuator configured to change a relative position of the stage with respect to at least one of the second lens and the detection unit.

6. The sample detection device of claim 1, wherein the second polarizer is oriented to block part of the emission light proceeding toward the second polarizer.

7. The sample detection device of claim 6, wherein the first direction is orthogonal to the second direction.

8. A non-transitory computer-readable storage medium including computer-executable instructions, wherein the instructions, when executed by a processor, cause the processor to perform a sample detection method using the sample detection device of claim 1, the method comprising:

emitting the incident light to the first polarizer to allow the first polarized light oscillating in the first direction to proceed toward the sample; and detecting the second polarized light to obtain an image of the sample based on the second polarized light.

9. A sample detection method using the sample detection device of claim 1, the method comprising:

emitting the incident light to the first polarizer to allow the first polarized light oscillating in the first direction to proceed toward the sample; and detecting the second polarized light to obtain an image of the sample based on the second polarized light.

10. The sample detection method of claim 9, further comprising:

obtaining the first image of the sample when the stage on which the sample is disposed is disposed at a first observation position;

obtaining the second image of the sample when the stage is disposed at a second observation position different from the first observation position; and obtaining the corrected image of the sample based on the first image and the second image.

11. The sample detection method of claim 10, further comprising:

moving the stage through an actuator to move a position of the sample from the first observation position to the second observation position.

12. The sample detection method of claim 10, further comprising:

giving a first weight to the first image and a second weight to the second image, wherein, the corrected image of the sample is corrected based on the first image given the first weight and the second image given the second weight.

* * * * *